United States Patent
Schmieding et al.

(10) Patent No.: US 7,238,189 B2
(45) Date of Patent: *Jul. 3, 2007

(54) ACL RECONSTRUCTION TECHNIQUE USING RETRODRILL

(75) Inventors: Reinhold Schmieding, Naples, FL (US); Giancarlo Puddu, Rome (IT)

(73) Assignee: Arthrex, Inc., Naples, FL (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/803,044

(22) Filed: Mar. 18, 2004

(65) Prior Publication Data

US 2004/0199166 A1 Oct. 7, 2004

Related U.S. Application Data

(60) Provisional application No. 60/455,391, filed on Mar. 18, 2003, provisional application No. 60/465,221, filed on Apr. 25, 2003.

(51) Int. Cl.
*A61B 17/16* (2006.01)

(52) U.S. Cl. ...................................................... 606/80

(58) Field of Classification Search .................. 606/80, 606/88, 96, 86, 72; 128/92, 892; 433/143, 433/147; 623/13.11–13.14
See application file for complete search history.

(56) References Cited

U.S. PATENT DOCUMENTS

| | | | |
|---|---|---|---|
| 4,781,182 A * | 11/1988 | Purnell et al. ................. | 606/96 |
| 4,787,377 A * | 11/1988 | Laboureau .................... | 606/84 |
| 5,211,647 A | 5/1993 | Schmieding | |
| 5,244,390 A * | 9/1993 | Lazzara et al. ............. | 433/143 |
| 5,269,786 A | 12/1993 | Morgan | |
| 5,320,626 A | 6/1994 | Schmieding | |
| 5,350,383 A | 9/1994 | Schmieding et al. | |
| 5,603,716 A | 2/1997 | Morgan et al. | |
| 5,676,544 A * | 10/1997 | Urban ......................... | 433/147 |
| 6,015,411 A | 1/2000 | Ohkoshi et al. | |
| 6,086,592 A * | 7/2000 | Rosenberg et al. ........... | 606/86 |
| 6,149,654 A | 11/2000 | Johnson | |
| 6,352,538 B2 * | 3/2002 | McGuire et al. .............. | 606/86 |
| 6,416,518 B1 * | 7/2002 | DeMayo ...................... | 606/96 |

OTHER PUBLICATIONS

Y. Ohkoshi et al., "A New Endoscopic Posterior Cruciate Ligament Reconstruction: Minimization of Graft Angulation," *Arthroscopy: J. of Arthroscopy and Related Surgery*, vol. 17, No. 3 (Mar. 2001), pp. 258-263.

(Continued)

*Primary Examiner*—Eduardo O Robert
*Assistant Examiner*—Richard Shaffer
(74) *Attorney, Agent, or Firm*—Dickstein Shapiro LLP

(57) ABSTRACT

Methods and apparatus for arthroscopic tenodesis using sockets in bone created by retrograde cutting. A cannulated pin is drilled through bone and into a joint space in the normal, antegrade direction, guided by a drill guide. A strand provided through the cannulated pin is used to draw a retrodrill cutter into the joint space. The retrodrill cutter is threaded onto the cannulated pin, which is turned for retrograde cutting of a socket into the bone. The method is used to form a pair of sockets in the joint, which accept the respective ends of a replacement graft. The graft is brought into position in the joint space using loops formed in the strands, in a manner similar to introduction of the retrodrill cutter. The reconstruction is completed by securing suture attached to the graft ends with a button implant installed at the bone surface.

8 Claims, 20 Drawing Sheets

OTHER PUBLICATIONS

Y. Ohkoshi et al., "Description of a New Endoscopic Posterior Cruciate Ligament Reconstruction and Comparison with a 2-Incision Technique," *Arthroscopy: J. of Arthroscopy and Related Surgery*, vol. 19, No. 8 (Oct. 2003), pp. 825-832.

\* cited by examiner

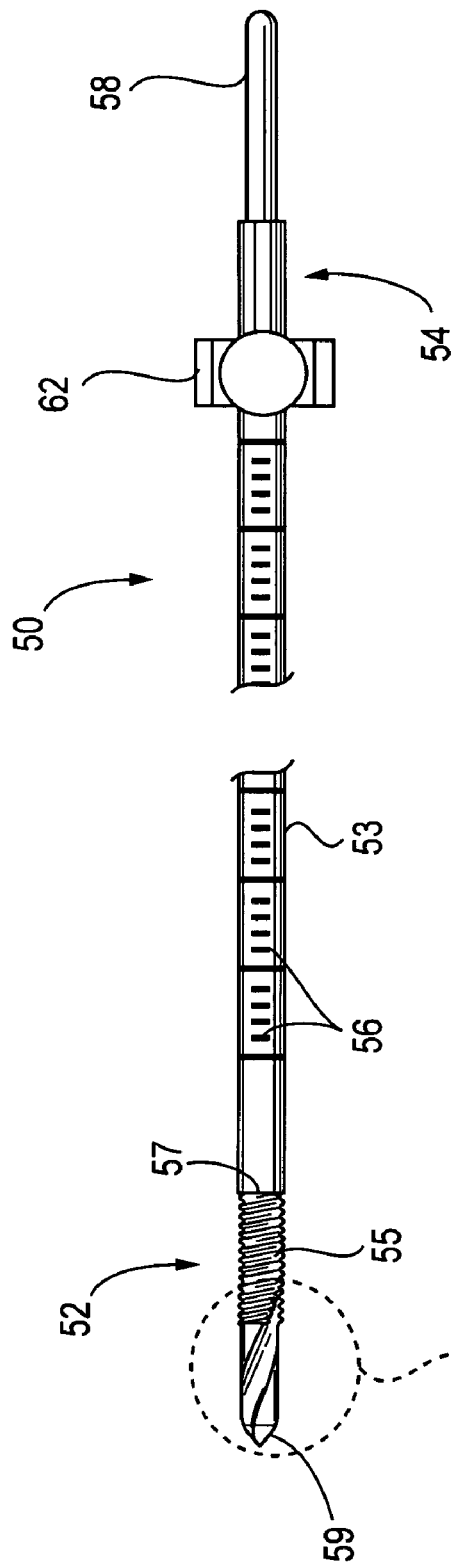
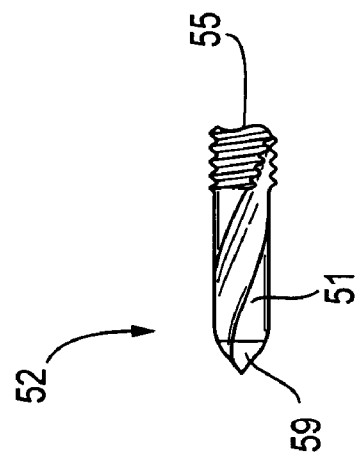
FIG. 2A
FIG. 2B

ACL RECONSTRUCTION TECHNIQUE USING RETRODRILL

This application claims the benefit of U.S. Provisional Application No. 60/455,391 filed Mar. 18, 2003, and U.S. Provisional Application No. 60/465,221, filed Apr. 25, 2003.

FIELD OF THE INVENTION

The present invention relates to the field of surgery and, more particularly, to methods of reconstructive knee surgery.

BACKGROUND OF THE INVENTION

Methods of anterior cruciate ligament (ACL) reconstruction (tenodesis) using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels is accomplished using a drill guide, examples of which are disclosed in U.S. Pat. Nos. 5,269,786 and 5,350,383, incorporated herein by reference.

One drawback of the described tenodesis methods is that forming the tibial tunnel involves removal of significant amounts of bone material. U.S. Pat. No. 5,603,716 to Morgan et al. discloses a technique for ACL reconstruction that avoids the above-noted problem by forming sockets in both the femur and the tibia using a coring bone harvester. The harvester is impacted into bone to a desired depth so that bone material collects as a bone core within the harvester tube. The bone core is extracted from the bone socket using a simultaneous twisting and pulling motion. Such harvesting of bone cores in the joint is technically difficult.

Accordingly, the need exists for a method of ACL reconstruction that provides tibial socket formation without the need for extracting a bone core to form a bone socket.

SUMMARY OF THE INVENTION

The present invention overcomes the disadvantages of the prior art and fulfills the needs noted above by providing techniques and apparatus for creating bone sockets by drilling in a retrograde manner.

According to one embodiment of the present invention, an apparatus for anterior cruciate ligament (ACL) reconstruction in a retrograde manner is provided in the form of a retrodrill cutter detachable from a retrodrill pin. The retrodrill cutter has a cannulated body provided with a plurality of cutting flutes. The retrodrill pin has a proximal end and a distal end, and a body provided with depth calibration markings. The distal end of the retrodrill pin is threaded for engagement with corresponding threads in the cannulation of the retrodrill cutter.

According to one embodiment of the present invention, anterior cruciate ligament (ACL) reconstruction is performed by creating femoral and tibial sockets created using a retrograde drilling technique. Retrodrill cutters are applied in a retrograde manner to drill into the femur and the tibia and create the femoral and tibial sockets, respectively.

The cutters are driven using thin (3 mm) retrodrill pins provided with depth markings. The proper anatomical positions inside the joint for creating the sockets are located, and precise alignment of the sockets is achieved using a C-ring drill guide. The cannulated retrodrill pin is inserted into a guide sleeve of the drill guide and drilled through the bone in the normal direction (antegrade) until contact is made with a marking hook of the drill guide, thus forming a narrow transosseous tunnel. A trocar is inserted into the cannulated retrodrill pin to form a pointed drill tip. The drill guide marking hook ends in a hook tip that is placed in the joint, and a mark 5 mm proximal of the hook tip is used to align the retrodrill pin.

A strand inserted through the cannulated retrodrill pin is retrieved through a surgical portal. The strand is attached to the retrodrill cutter, which is drawn into the joint by pulling the strand, assisted by a grasper or a shoehorn cannula. The retrodrill cutter is placed into the anatomical joint space and positioned so that the cannulated retrodrill pin can be threaded into the retrodrill cutter. Once secured to the retrodrill cutter, the retrodrill pin is rotated and retracted through the joint surface and into bone to the proper depth as measured on the outside of the knee by the depth markings on the retrodrill pin. After each socket is formed, the retrodrill cutter is removed from the retrodrill pin by applying a reverse drilling motion to the retrodrill pin while grasping the cutter. The retrodrill pins are left in position for use in subsequent surgical steps.

A graft, such as a composite femoral bone/tendon allograft, is prepared to have a diameter corresponding to the diameter of the femoral and tibial sockets. The length of the graft equals the sum of the lengths of the femoral and tibial sockets plus the joint space distance between the two socket openings. Loops formed in the strands are pulled out through a surgical portal and connected to the ends of the graft. The strands are pulled, drawing the ends of the graft into the joint. The loops of the strands will not pass through the cannulated retrodrill pins and instead are drawn out as the retrodrill pins are retrograded by hand with a Jacob's chuck handle, for example, pulling the strands through the respective transosseous tunnels. The graft is drawn into the joint, with the assistance of a shoehorn slotted cannula or an ACL grasper, until the ends of the graft are positioned fully into the sockets.

Once the graft has been pulled fully into the femoral and tibial sockets, graft tensioning and fixation are carried out. Fixation preferably is carried out by securing the strands using a button implant inserted into the openings of the narrow tunnels at the bone surface.

Other features and advantages of the present invention will become apparent from the following description of the invention which refers to the accompanying drawings.

BRIEF DESCRIPTION OF THE DRAWINGS

FIGS. 2A and 2B illustrate a retrodrill pin according to the present invention;

DETAILED DESCRIPTION OF THE PREFERRED EMBODIMENT

The present invention provides retrodrill techniques and apparatus for forming femoral and tibial bone sockets in a retrograde manner during ligament reconstruction, for example, anterior cruciate ligament (ACL) reconstruction. The present invention also provides methods of graft preparation, insertion and fixation employed in connection with the femoral and tibial sockets of the present invention.

Figure 1A:
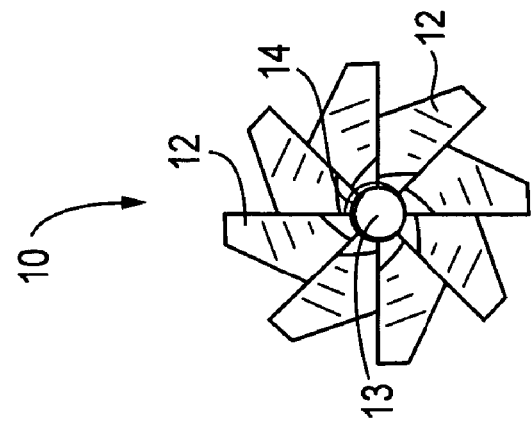
FIGS. 1A–1C illustrate a retrodrill cutter according to the present invention.
Figure 1B:
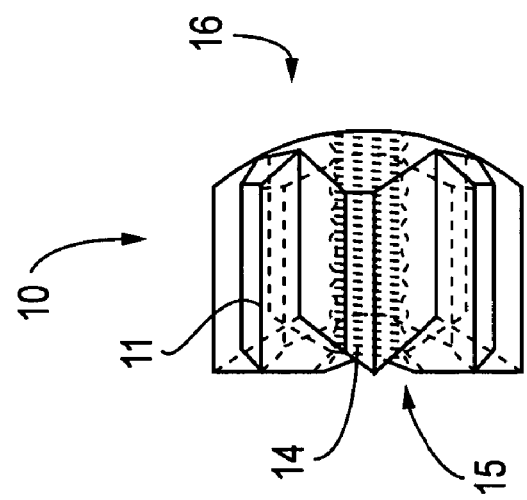
Figure 1C:
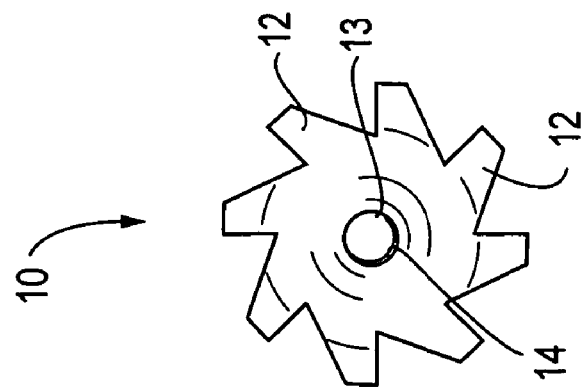

Referring now to the drawings, where like elements are designated by like reference numerals, FIGS. 1–2 illustrate a retrodrill cutter 10 (FIGS. 1A–1C) which is adapted to be threadingly engaged with a cannulated retrodrill pin 50 (FIGS. 2A–2C).

Referring to FIGS. 1A–1C, the retrodrill cutter 10 features a cylindrical body 11 having a plurality of cutting teeth 12 radiating symmetrically. A cannulation 13 through body 11 is provided with internal screw threads 14. Cutting teeth 12 have edges extending radially from cannulation 13 on a proximal cutting face 15, seen in plan view in FIG. 1A. The edges of cutting teeth 12 continue axially along the side of the retrodrill cutter 10, which is oriented orthogonally to proximal cutting face 15. The edges end at a smooth, rounded distal end 16 of retrodrill cutter 10. Retrodrill cutter 10 is provided in a selected diameter corresponding to graft size as discussed further below.

Referring to FIGS. 2A–2B, retrodrill pin 50 features a fluted region 51 formed on distal end 52 of cannulated body 53, as shown in detail in FIG. 2B. Cannulated body 53 has a proximal end 54. The cannulated body 53 is provided with screw threads 55 at distal end 52. The screw threads 55 are fashioned to engage corresponding threads 14 of retrodrill cutter 10. Accordingly, the outer diameter of threaded region 55 closely approximates the diameter of cannula 13 of the retrodrill cutter 10, to allow secure engagement of the outer threaded region 55 with the inner threads 14 of retrodrill cutter 10.

Retrodrill pin 50 features visible calibrated depth markings 56 lazed onto the cannulated body 53. Between threads 55 and depth markings 56, a shoulder 57 is formed to provide a stop where threads 55 end. The lumen of cannulated body 53 accepts a trocar 58 having a pointed tip 59. When the trocar is removed, a strand can be passed through the lumen of the cannulated body 53, as described below in greater detail. The proximal end 54 of cannulated body 53 is configured for chucking into a rotary driver (not shown). The distal end 52 of cannulated body 53 is open at the tip to expose the pointed end 59 when the trocar 58 is inserted into the cannulated body 53, as when drilling the assembled retrodrill pin 50 into bone. Retrodrill pin 50 includes a setscrew collar 62 for securing the trocar 58 in the cannulated body 53.

An exemplary method of using the retrodrill pin 50 and the retrodrill cutter 10 to create a femoral socket 100 of the present invention is described below with reference to FIGS. 3–9, which illustrate a schematic anterior view of a knee in which ACL reconstruction is performed according to the present invention. In the following embodiment, a femoral socket 100 (shown completed in FIG. 9) is formed in a femur 66.

Figure 3:
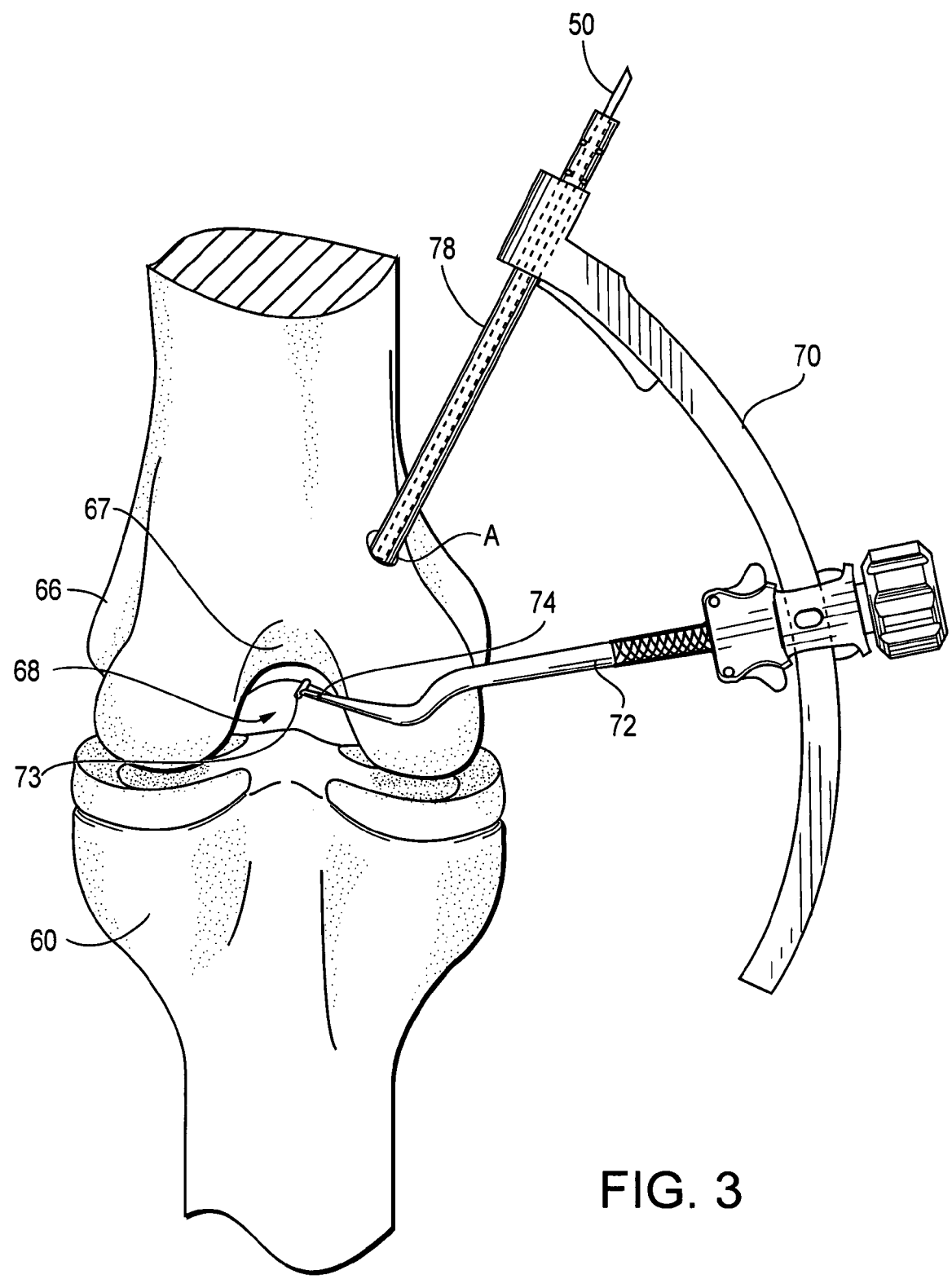
FIG. 3 schematically illustrates an initial stage in the formation of a femoral socket according to the present invention.

Referring to FIG. 3, femoral tunnel alignment is obtained using a long adapter drill guide 70, such as an Arthrex C-Ring cross-pin drill guide, which is disclosed in U.S. Pat. Nos. 5,350,383 and 5,918,604, the disclosures of which are incorporated by reference. The drill guide 70 is secured to the lateral thigh, over femur 66 and lateral to intercondylar notch 67, as shown in FIG. 3. Sleeve 78 of the adapter drill guide 70 is placed through a lateral portal A and marking hook 72 is hooked in the "over-the-top" position. Hook 72 includes a laser mark 74 located 5 mm proximate (anterior) to tip 73 of the marking hook 72, to ensure placement of the retrodrill pin 50 anterior to the intercondylar notch 67.

Once the anatomical position in the joint for the femoral socket has been identified, and the appropriate drilling angle has been selected on the drill guide 70, femoral retrodrill pin 50, with the installed trocar 58, is inserted through sleeve 78, as shown in FIG. 3. The femoral retrodrill pin 50 is drilled through the lateral femur until contact is made with the marking hook 72 of long adapter drill guide 70.

Figure 4:
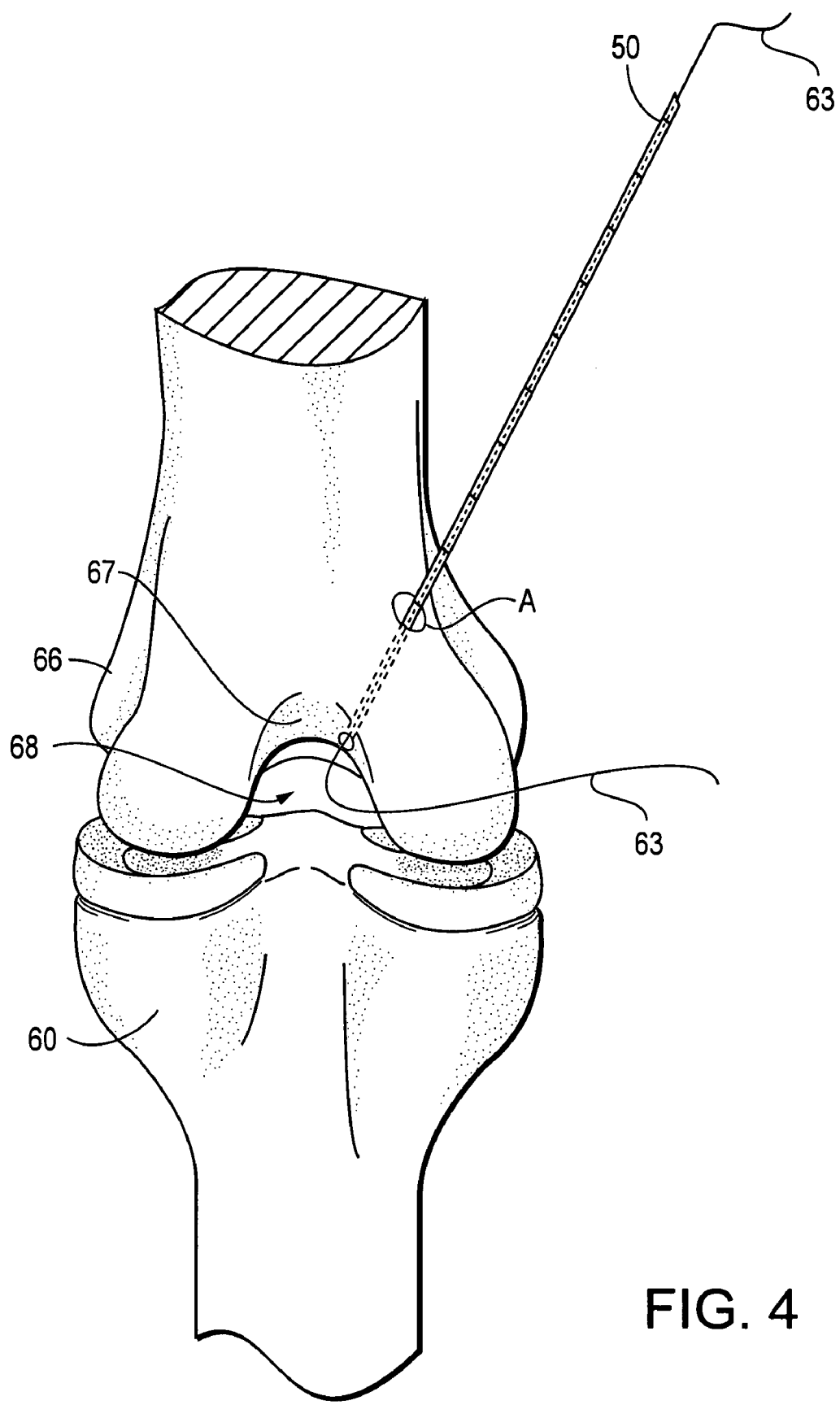
FIG. 4 schematically illustrates the formation of a femoral socket at a stage subsequent to that shown in FIG. 3.
Figure 5:
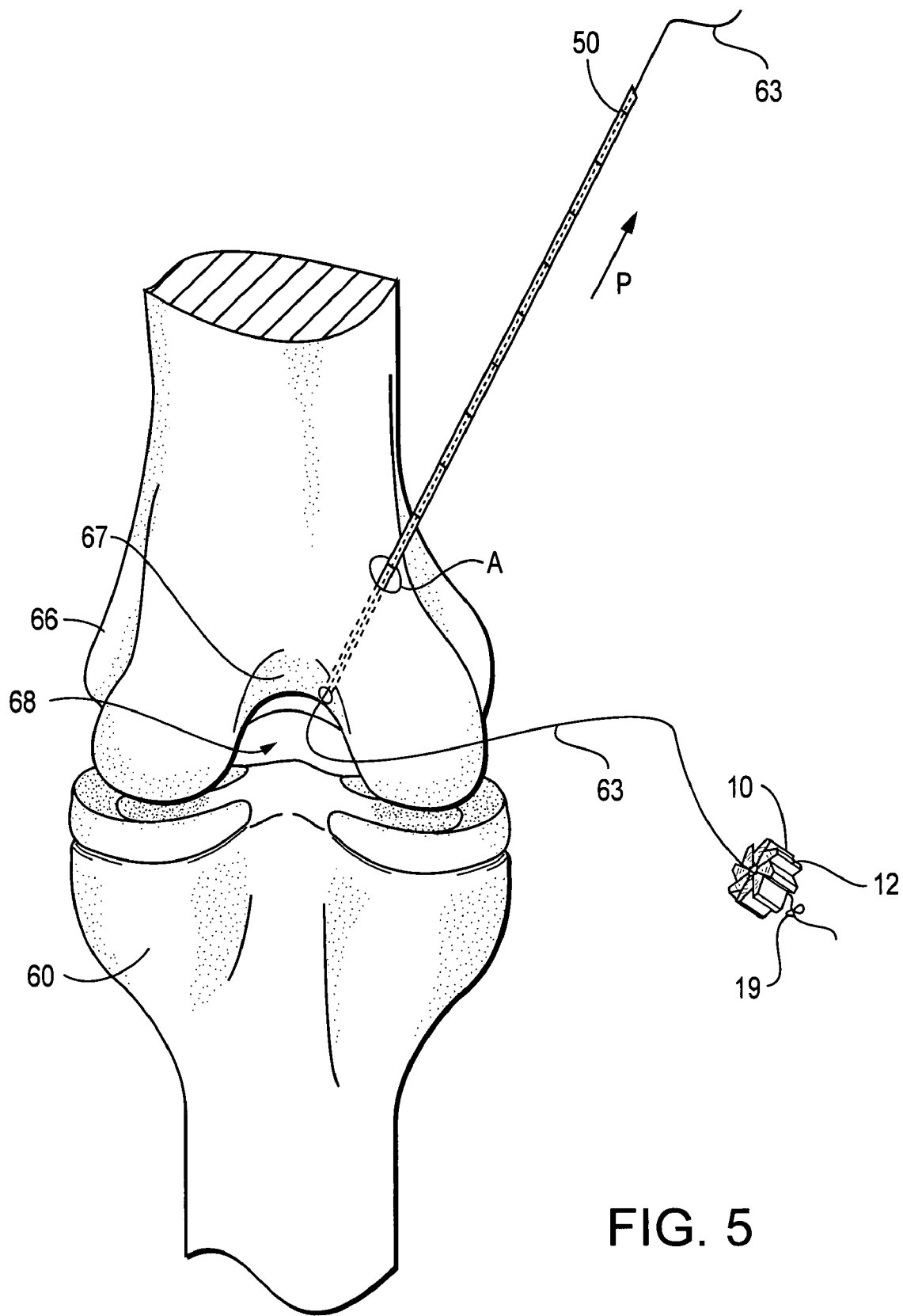
FIG. 5 schematically illustrates the formation of a femoral socket at a stage subsequent to that shown in FIG. 4.
Figure 6:
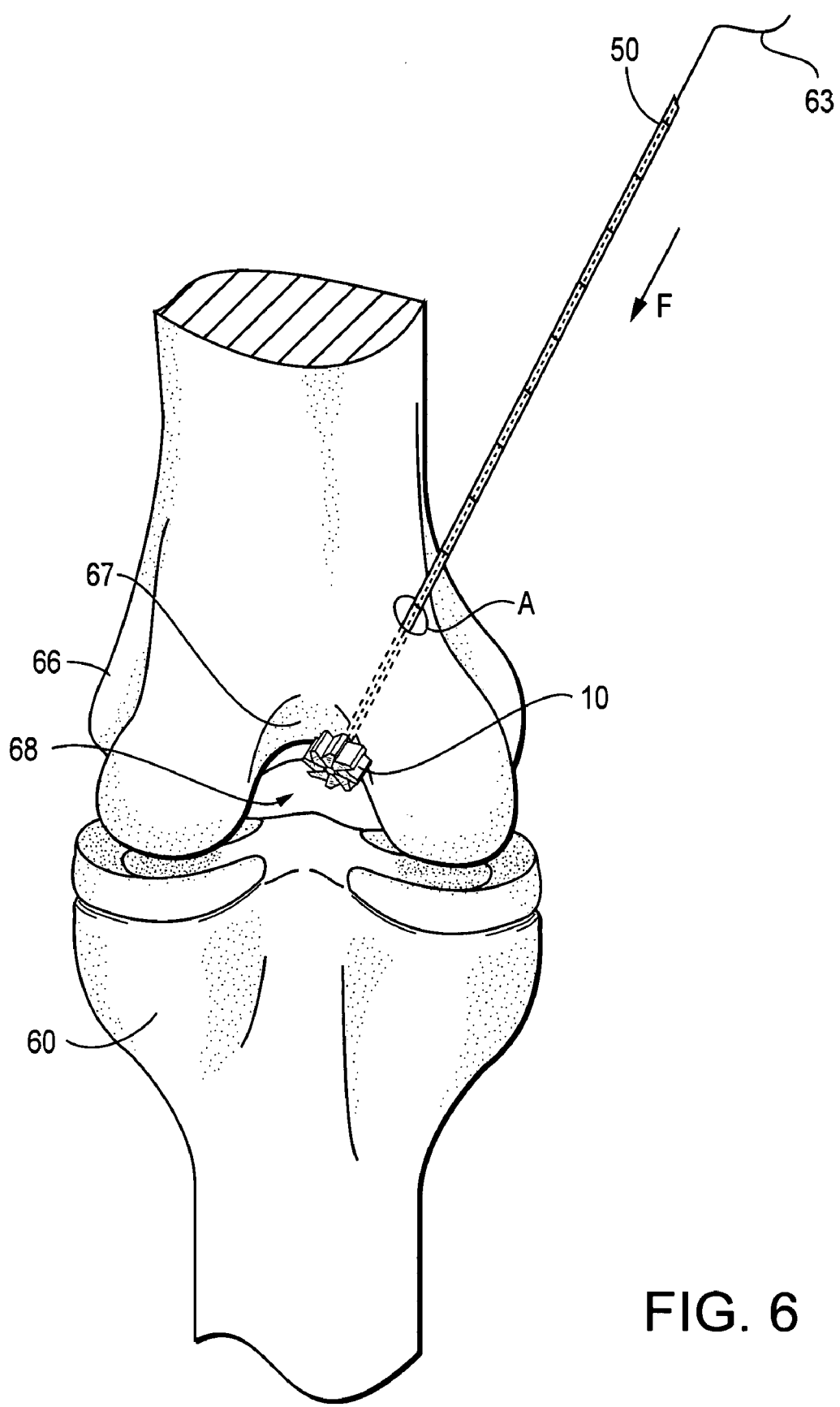
FIG. 6 schematically illustrates the formation of a femoral socket at a stage subsequent to that shown in FIG. 5.
Figure 7:
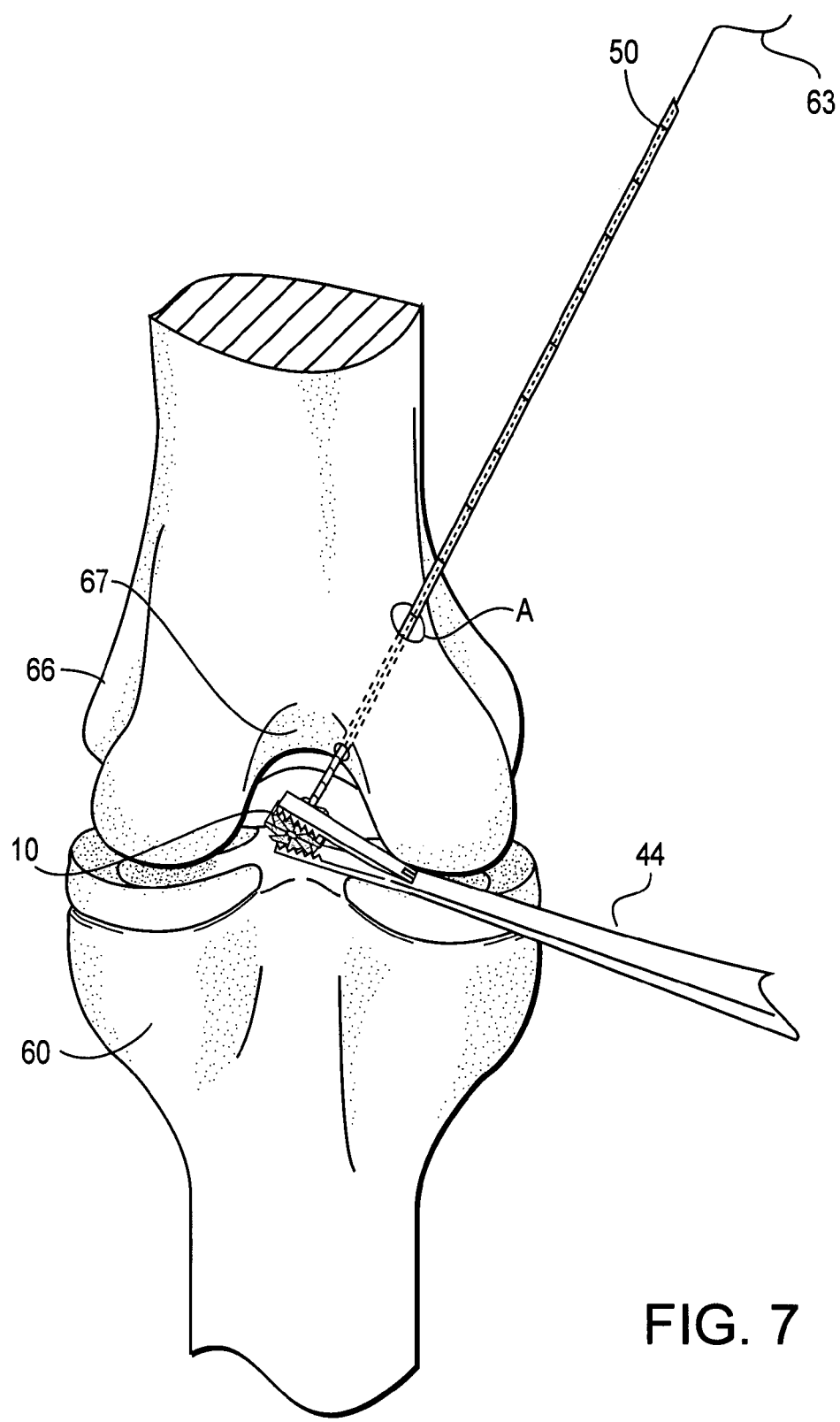
FIG. 7 illustrates a grasper employed in connection with the retrodrill cutter of the present invention.

Referring to FIG. 4, drill guide 70 is removed, and a strand 63, preferably a stiffened suture such as FiberStick (a high strength suture product with a stiff tip, sold by the assignee, Arthrex, Inc.), or a wire, is inserted through the retrodrill pin 50 into the joint space 68. A suture retriever is introduced to retrieve the inserted end of the strand 63 and pull it out through a medial portal. The strand 63 is placed through the cannula 13 of the retrodrill cutter 10 and retained using a Mulberry knot 19 tied in the strand on the rounded distal side 16 of the retrodrill cutter 10, as shown in FIG. 5. The strand 63 is pulled in the direction of arrow "P" of FIG. 5 to draw the retrodrill cutter 10 through the medial portal and into the joint space 68. Proper orientation of the retrodrill cutter 10 can be achieved using a grasper 44 (FIG. 7) or a shoehorn cannula. The retrodrill cutter 10 is positioned to be threaded onto the femoral retrodrill pin 50 by turning and advancing the retrodrill pin 50 in the relative direction of arrow F (FIG. 6) (antegrade) into the cannulation 13 of retrodrill cutter 10.

Figure 8:
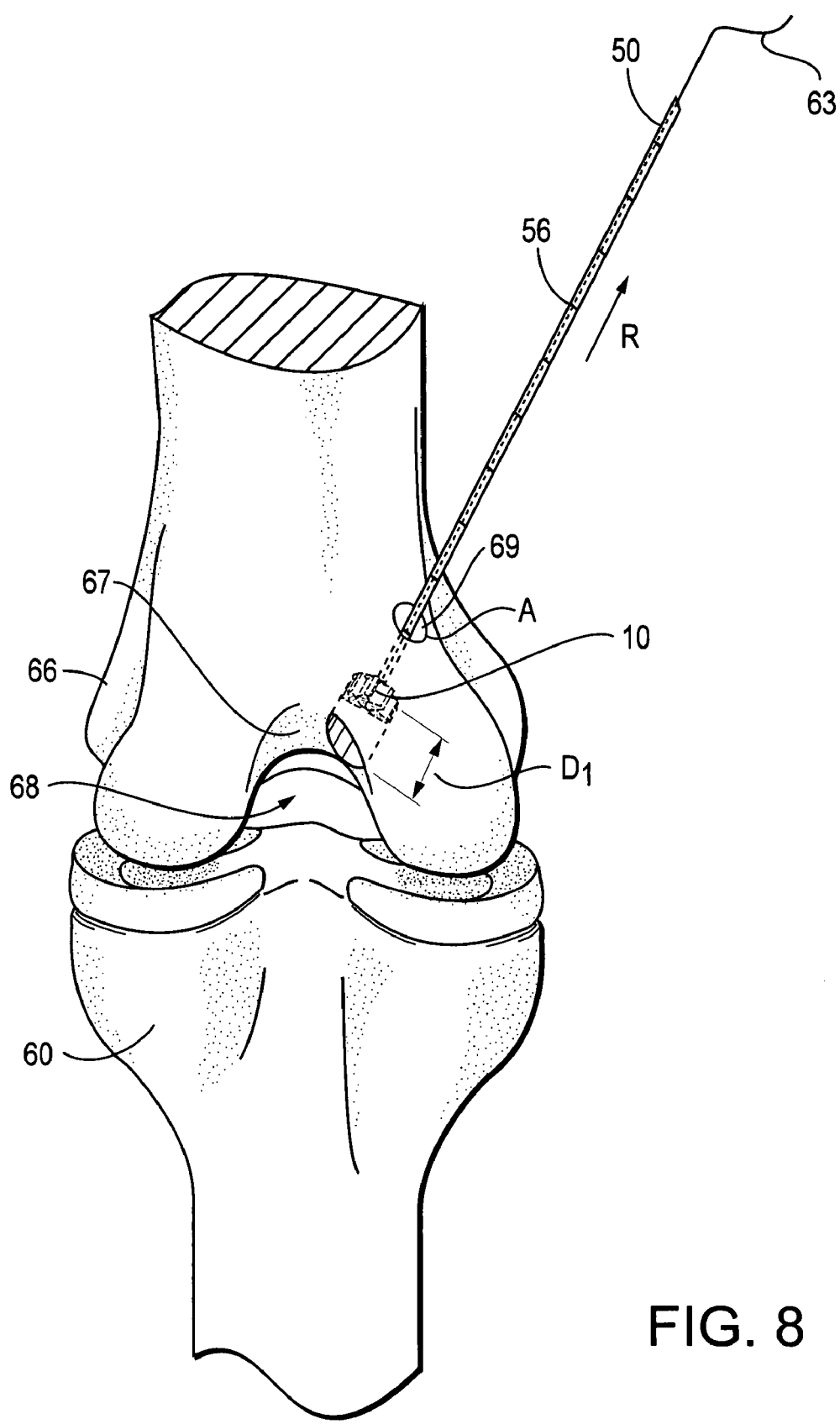
FIG. 8 schematically illustrates the formation of a femoral socket at a stage subsequent to that shown in FIG. 6.

Referring to FIG. 8, once securely engaged within the retrodrill cutter 10, the retrodrill pin 50 is rotated with a power driver (not shown) and retracted (retrograde) to cut through the femoral joint surface and into bone to create femoral socket 100. A desired depth $D_1$, preferably 25 mm., is obtained by reading the markings 56 on the femoral retrodrill pin 50, recorded relative to the skin femoral surface prior to and during socket formation.

Figure 9:
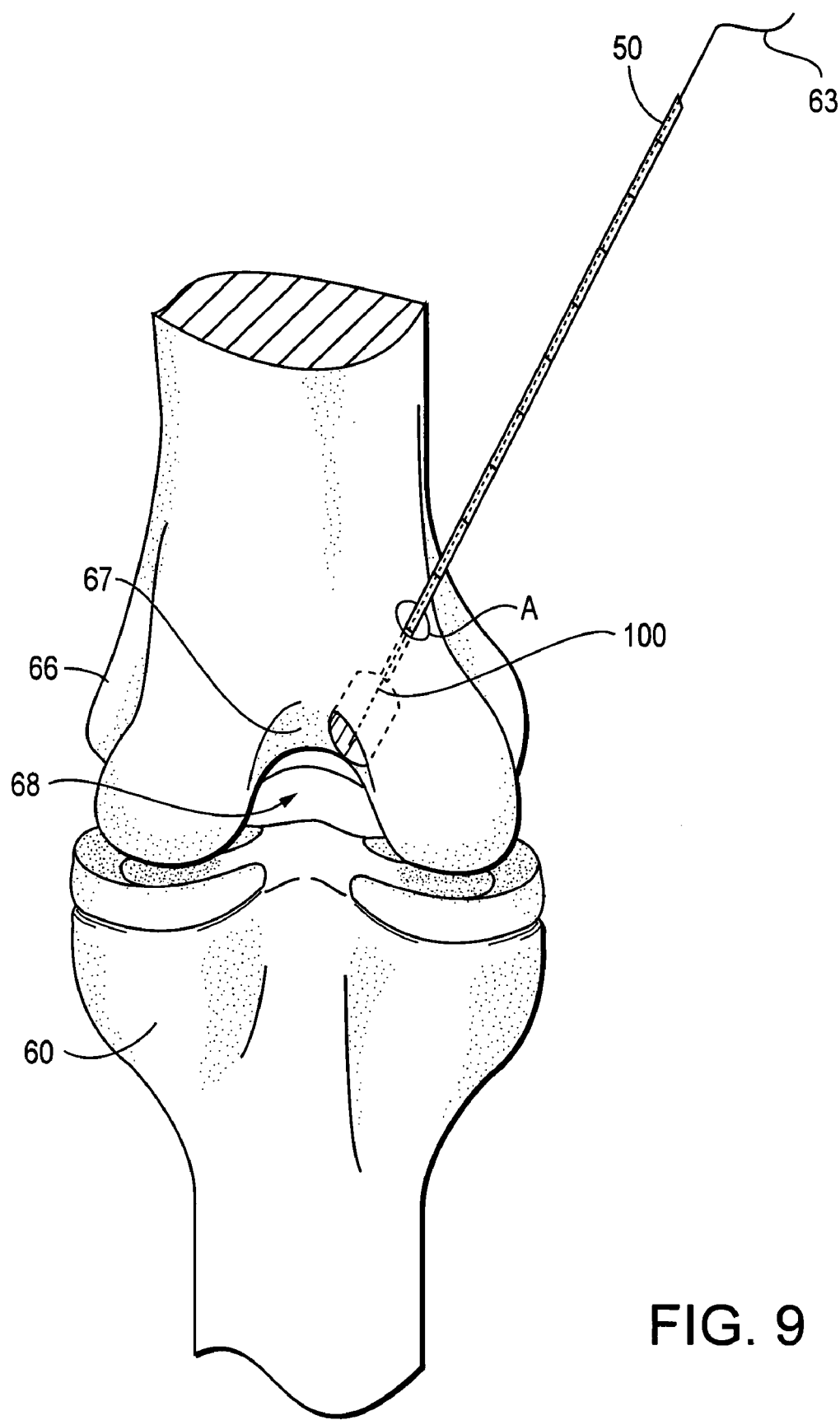
FIG. 9 schematically illustrates the formation of a femoral socket at a stage subsequent to that shown in FIG. 8.

Once the desired socket depth is achieved, the retrodrill cutter 10 is pushed distally (antegrade) out of the socket and back into the joint space 68. Using an instrument such as grasper 44 (FIG. 7) to hold the retrodrill cutter 10, the retrodrill pin 50 is unscrewed from the retrodrill cutter 10 in the direction of arrow R of FIG. 8, and the retrodrill cutter 10 removed from the joint space through the medial portal, leaving retrodrill pin 50 in position as illustrated in FIG. 9. Strand 63 also remains and, during removal of retrodrill cutter 10, acts as a safety line should the retrodrill cutter 10 become lost or disengaged from the grasper 44 during removal.

Figure 10:
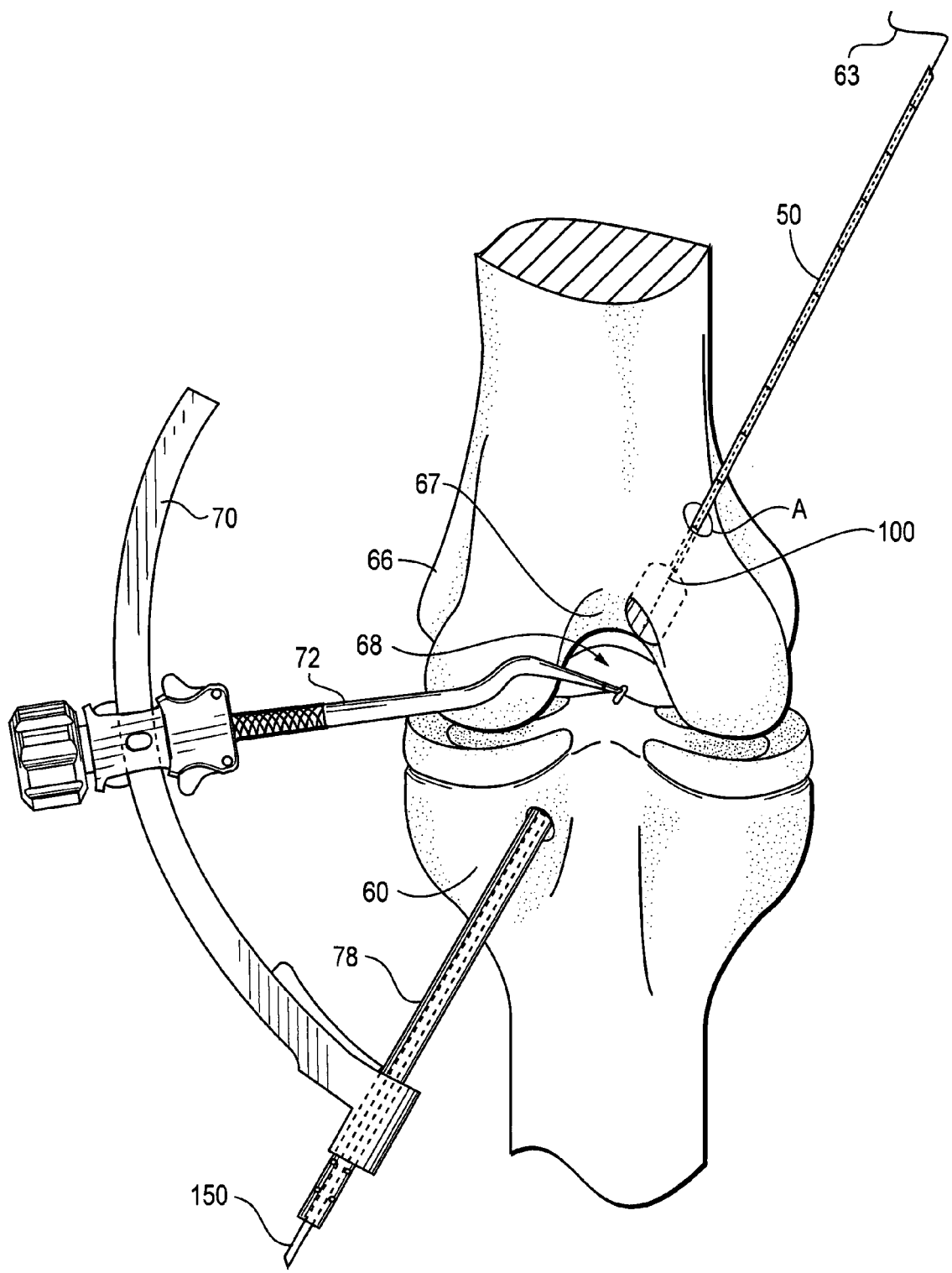
FIG. 10 schematically illustrates an initial stage in the formation of a tibial socket according to the present invention.

Subsequent or prior to the formation of the femoral socket 100, a tibial socket 200 (shown completed in FIG. 11) is formed by a method similar to that described above for the formation of the femoral socket 100. Accordingly, anatomical position and alignment are established for creation of the tibial socket 200 using the drill guide 70. Tibial retrodrill pin 150 is inserted through guide sleeve 78, as shown in FIG. 10. The tibial retrodrill pin 150, with inserted trocar, is drilled through the tibia 60 until contact is made with the marking hook 72 of long adapter drill guide 70. With the retrodrill pin in position, the guide 70 is removed from pin 150, which remains in place in the small tibial tunnel.

Creation of the tibial socket 200 continues in a manner similar to that for creating femoral socket 100. The trocar is removed from retrodrill 150, and is replaced by a stiffened suture strand 163, preferably FiberStick. A grasper 44 or a suture retriever is inserted into the joint space 68 to retrieve the inserted end of the strand 163 and pull it out through the medial portal. The strand 163, passed through the cannula 13 of the retrodrill cutter 10 and retained using a Mulberry knot, is pulled to draw the retrodrill cutter 10 into the joint space 68. The retrodrill cutter 10 is positioned using a grasper and tibial retrodrill pin 150 is threaded into the cannulation 13 of the retrodrill cutter 10.

Figure 11:
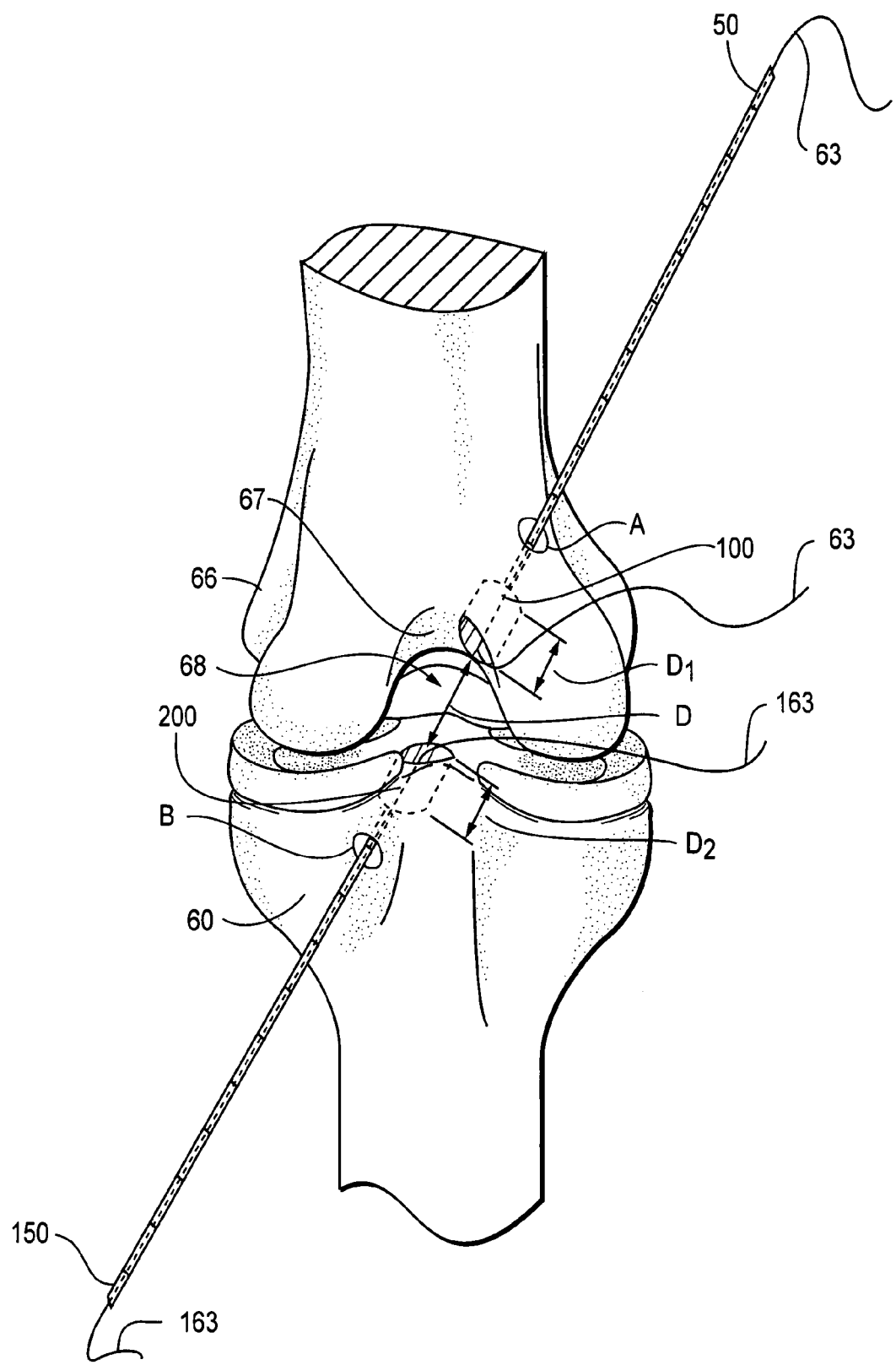
FIG. 11 schematically illustrates the formation of a tibial socket at a stage subsequent to that shown in FIG. 10.

Once engaged with the retrodrill cutter 10, the tibial retrodrill pin 150 is rotated and retracted to drill a socket 200 in the tibia 60 to a desired depth $D_2$, preferably 25 mm., as shown in FIG. 11. The retrodrill 10 is then pushed distally to exit the socket. A grasper is used to disengage the drill from the pin, and the retrodrill 10 is removed from the joint. The tibial retrodrill pin 150 remains in position, as shown in FIG. 11.

A soft tissue graft or a composite femoral bone/tendon allograft is prepared for insertion and fixation into the femoral and tibial sockets 100, 200. The graft is selected so that its diameter corresponds to the diameters of the femoral and tibial sockets 100, 200. Alternatively, the correct diameter of the retrodrill cutter 10 may be selected to correspond to the diameter of a previously-prepared graft 300, illustrated in FIG. 12. The graft 300 has a length L (FIG. 12) equal to the summed lengths of the femoral and tibial sockets plus the joint length between the two sockets. For example, assuming that the length $D_1$ (FIG. 11) of the femoral socket 100 is about 25 millimeters, the length $D_2$ (FIG. 11) of the tibial socket is about 25 millimeters, and the length D (FIG. 11) between the two sockets is about 28 millimeters, the total length L of the graft 300 is about (25+25+28) millimeters, or about 78 millimeters.

Graft 300 is formed from soft tissue according to an exemplary embodiment of the present invention. The graft 300 is folded in half and whip stitched at the graft proximal end 301 and distal bundle ends 302, 304. The graft is marked 25 mm from the graft proximal end 301, for example, corresponding to the depth D, for the femoral socket 100. A joint space length L of 28 mm, for example, is marked further down the graft 300. The two distal graft bundles are measured to 25 mm, for example, corresponding to the depth $D_2$ for the tibial socket.

Figure 12:
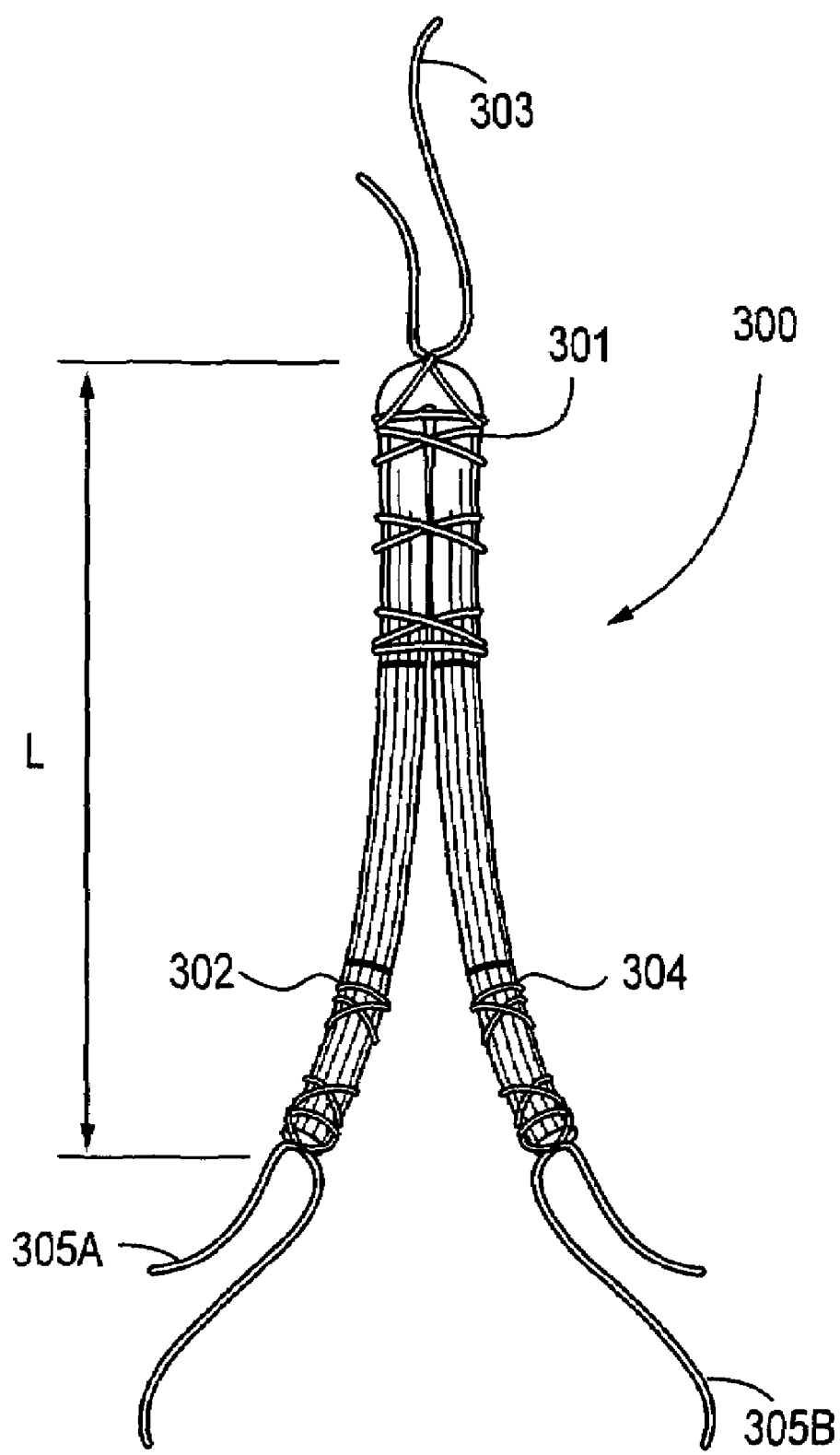
FIG. 12 illustrates a graft to be employed in connection with a femoral and tibial sockets of the present invention, and in accordance with a method of graft fixation of the present invention.

Each of the ends of the graft 300 is securely whip-stitched independently with one set of strands 303 and another set of strands 305A and 305B, as illustrated in FIG. 12. Preferably, at least the strands 305A and 305B are visually distinguishable. The diameter of the graft is measured, for example using a graft sizing block (not shown), to determine the diameter of the femoral and tibial sockets.

Figure 13:
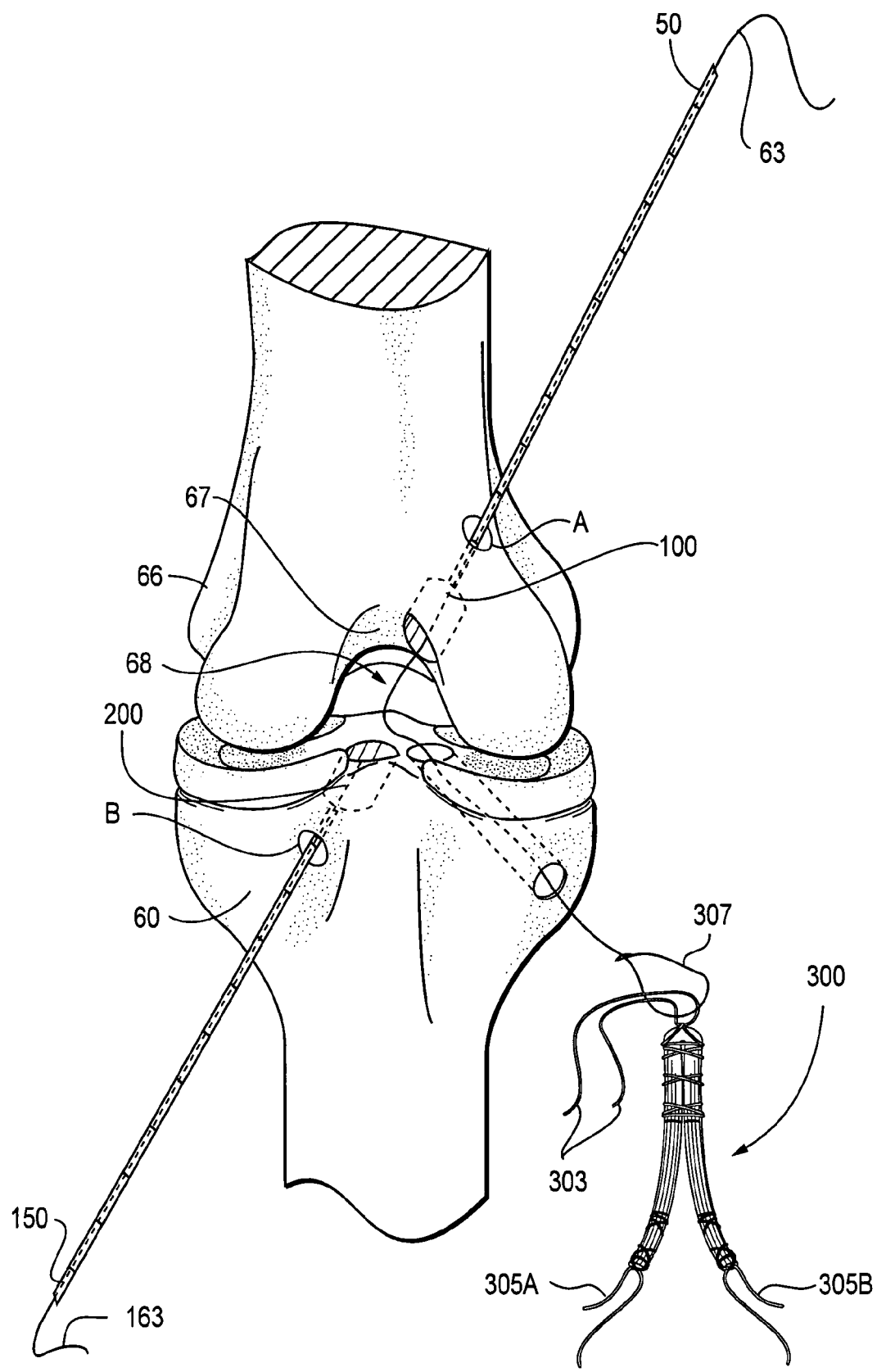
FIG. 13 illustrates a schematic view of a knee joint undergoing graft insertion according to an embodiment of the present invention.
Figure 14:
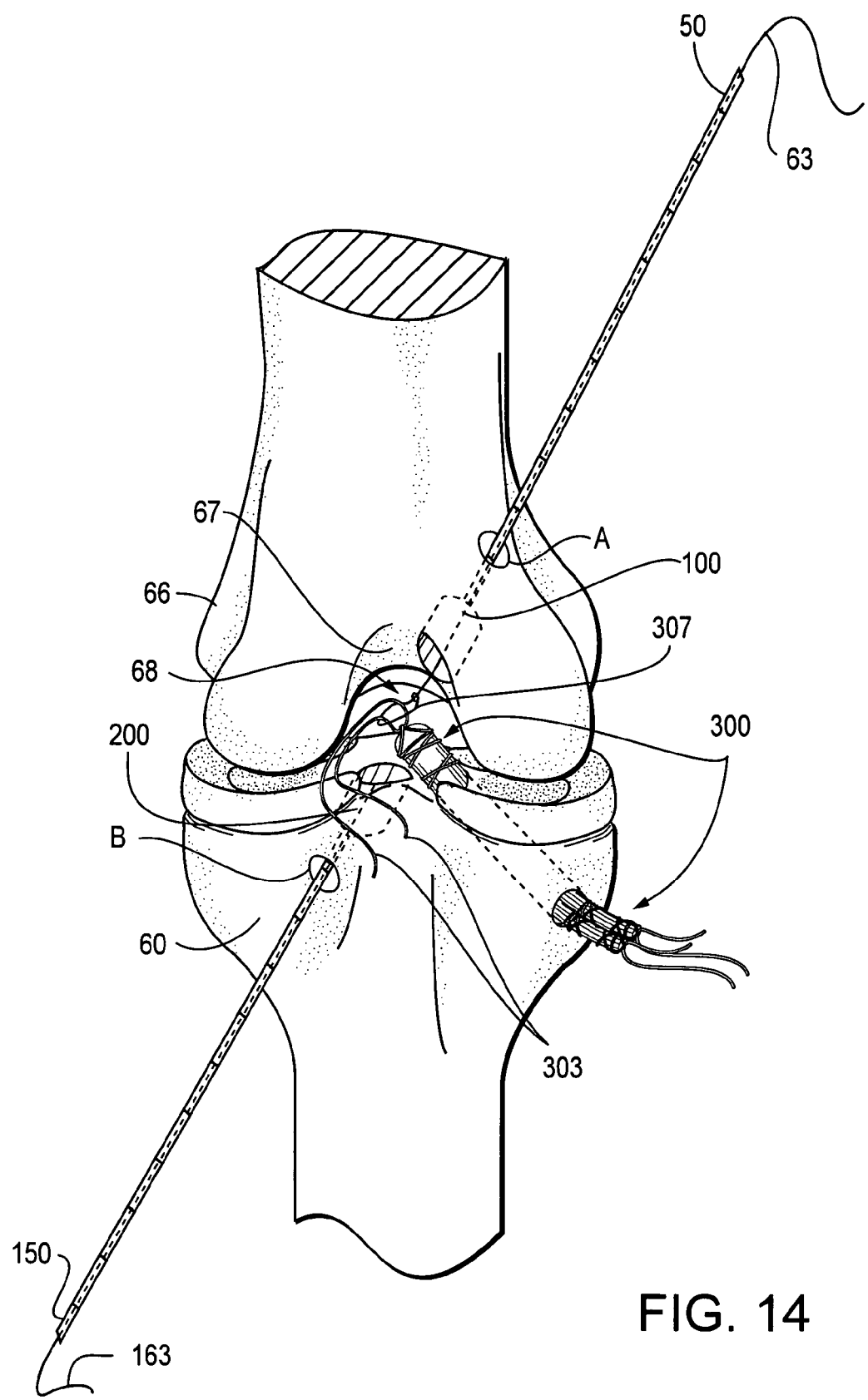
FIG. 14 is a close-up illustration of the knee joint of FIG. 13 at a stage of graft insertion and fixation subsequent to that shown in FIG. 13.
Figure 15:
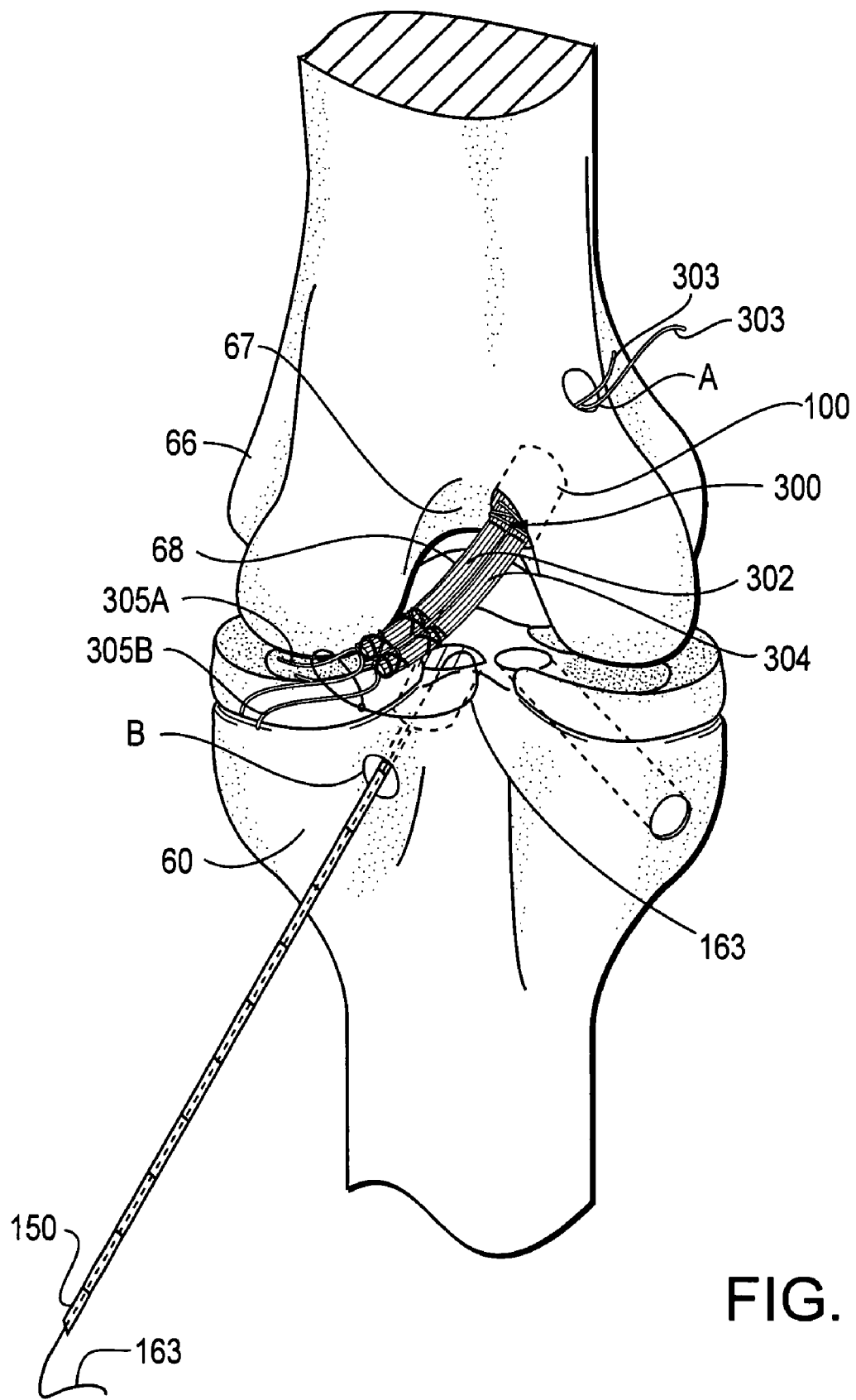
FIG. 15 is a close-up illustration of the knee joint of FIG. 13 at a stage of graft insertion subsequent to that shown in FIG. 14.

Installation of the graft is illustrated schematically in FIGS. 13–18. A loop 307 is formed in the femoral strand 63 and pulled out the medial portal to use as a transport for the proximal graft suture strands 303. The set of graft suture strands 303 is passed through the loop 307 and pulled into the joint, as shown in FIGS. 13 and 14, through the femoral socket, and out through the lateral thigh. Referring to FIG. 15, graft 300 is pulled into the femoral socket 100 up to the 25 mm mark on the graft 300 to ensure complete seating.

Figure 16:
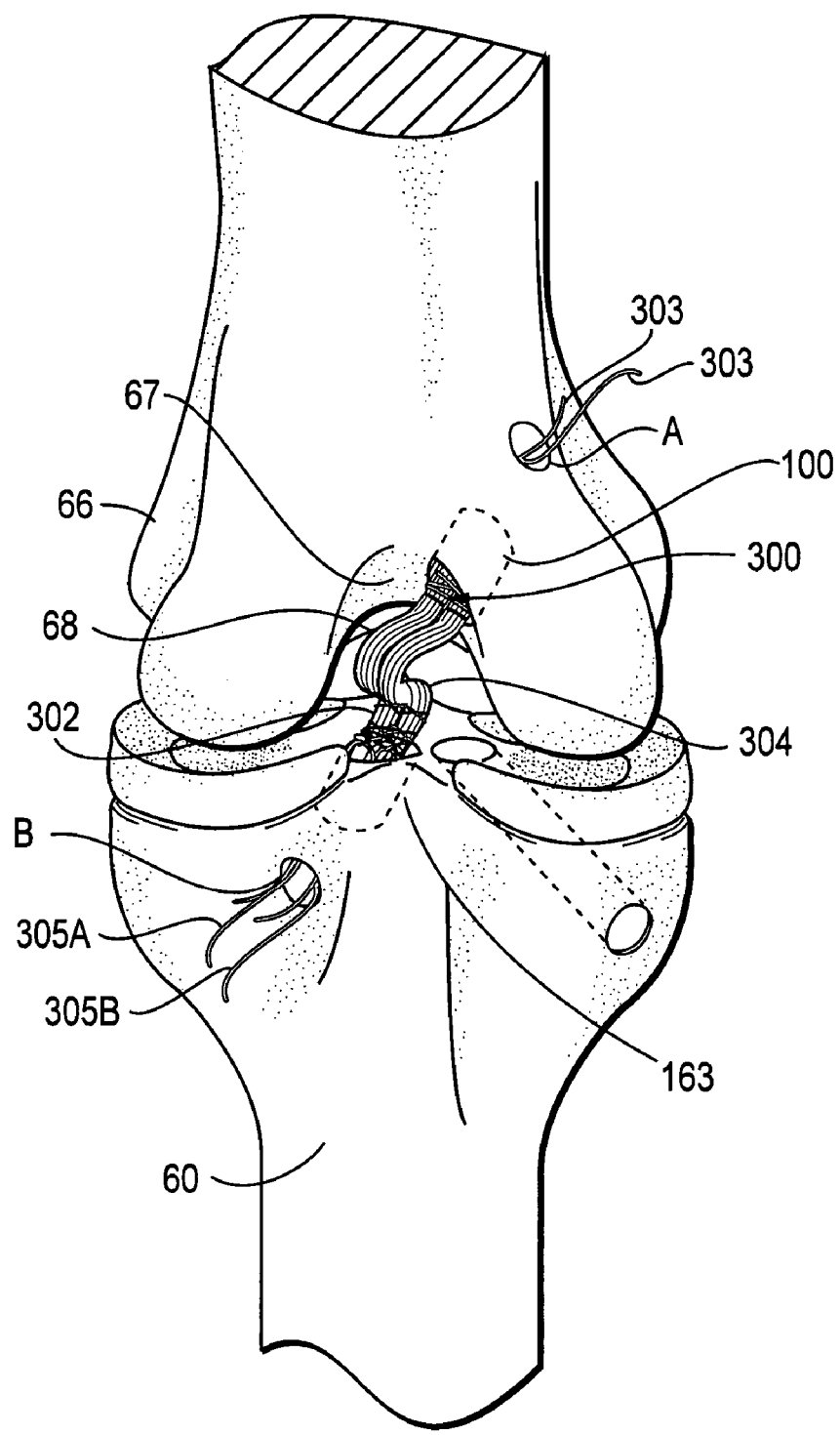
FIG. 16 is a close-up illustration of the knee joint of FIG. 13 at a stage of graft insertion subsequent to that shown in FIG. 15.
Figure 17:
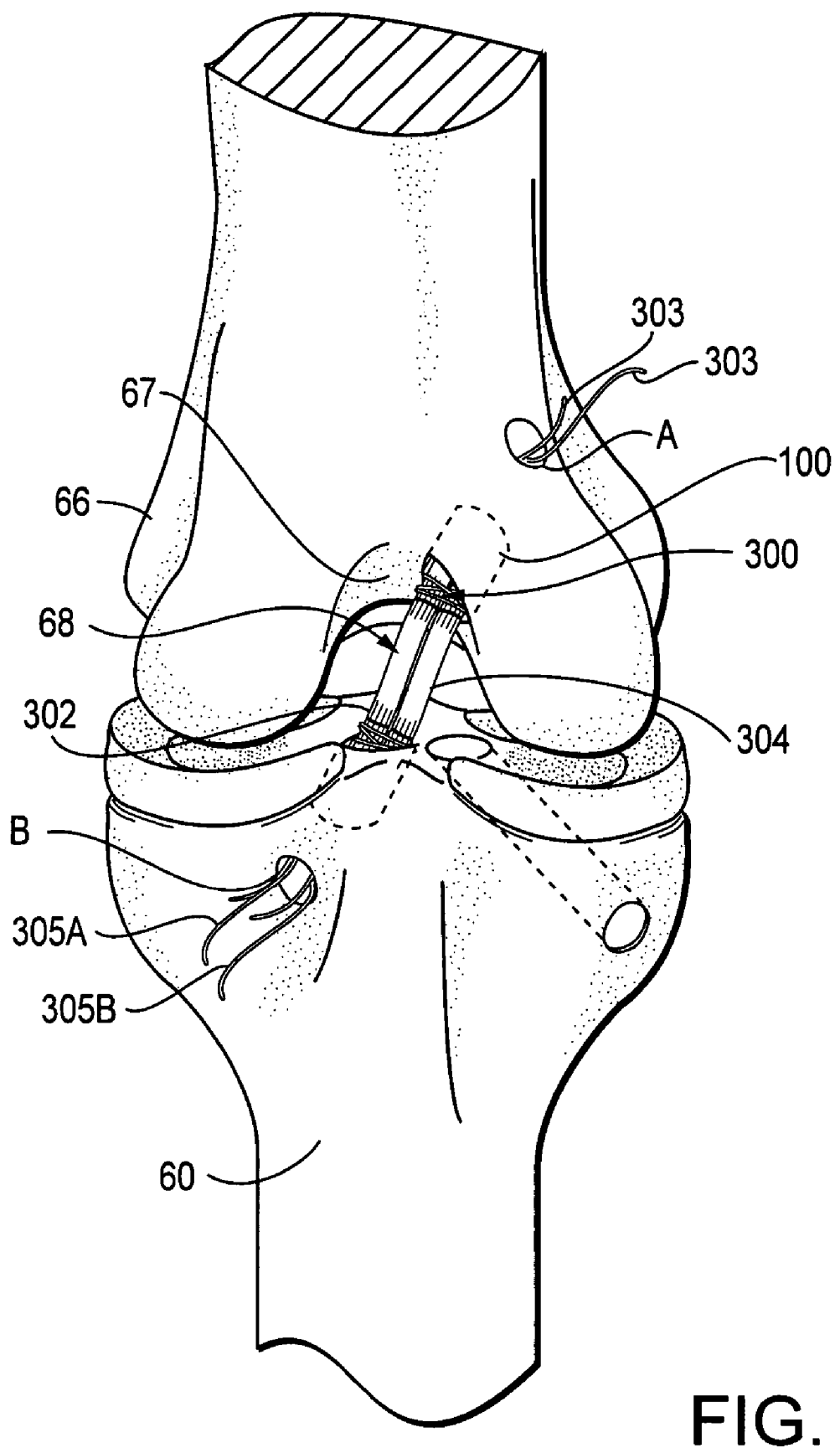
FIG. 17 is a close-up illustration of the knee joint of FIG. 13 at a stage of graft insertion subsequent to that shown in FIG. 16.

Insertion of bundles 302 and 304 of graft 300 into tibial socket 200 proceeds similarly. A loop formed in tibial strand 163 around strands 305A and 305B is used to pull the strands 305A and 305B into the tibial socket 200, as shown in FIG. 16. Strands 305A and 305B are brought out through the tibial portal. Both distal bundles 302, 304 of the graft are seated into the tibial socket up to the pre-marked line, as shown in FIG. 17.

Figure 18:
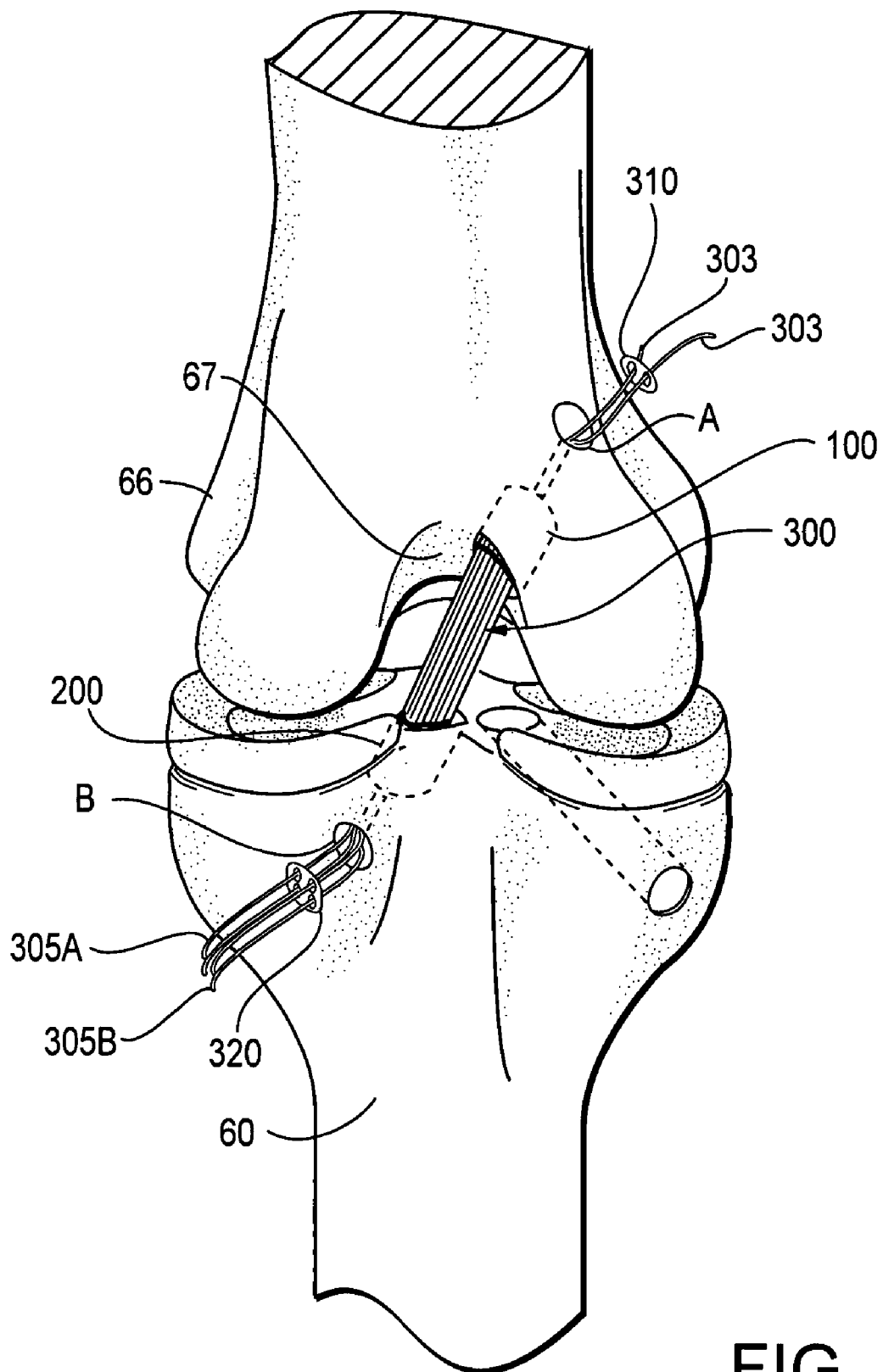
FIG. 18 illustrates a schematic view of a knee joint having undergone graft insertion and prior to graft fixation according to an embodiment of the present invention.
Figure 19:
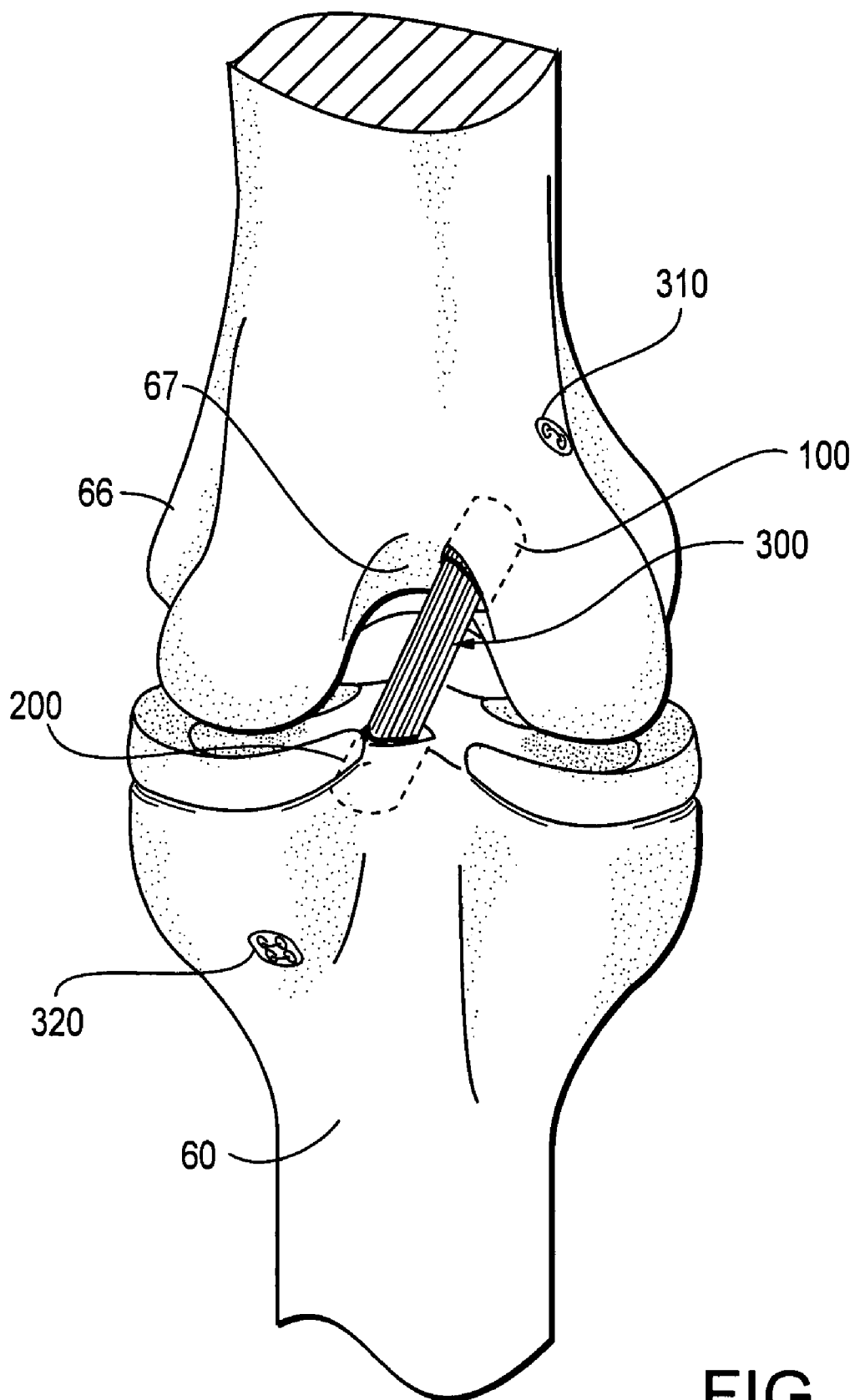
FIG. 19 illustrates a schematic view of a knee joint having undergone graft insertion and fixation according to an embodiment of the present invention.

Referring to FIG. 18, graft 300 is shown fully inserted, the femoral and tibial retrodrill pins 50, 150 having been withdrawn and strands 303, 305A, and 305B extending through the respective transosseous femoral and tibial tunnels 100, 200. With the ends of the graft 300 seated fully into the femoral and tibial sockets 100, 200, graft tensioning and fixation is carried out. A button 310 is attached to the two ends of strand 303. A Crabclaw knot pusher is used to advance the button 310 through the femoral portal down to the femoral bone surface. Multiple knots are tied to secure the button 310 with the knot pusher instrument. The button 310 includes two through-holes to accommodate the suture, and is made of a biocompatible material, typically a polymer, preferably PEET.

A second button 320 is attached to each end of strands 305A and 305B. Three non-reversing half hitches are tied and pushed down to the bone with a crabclaw knot pusher. Tension preferably is applied separately to each of the two tibial bundles, one with the knee in flexion and one with the knee in extension, as is known in the art. The post end of strands 305A is passed through a suture tensioner (not shown). The suture tensioner securely holds the button onto the bone, and the strands 305A is secured through slots and a holding screw at the end of the suture tensioner. The tensioning screw is turned to tension graft 300 and tighten the knots with the knee in the appropriate flexion/extension. As the surgeon determines the proper tensioning, quantified with load markings on the tensioner handle, a reversing half hitch is tied over the shaft of the tensioner and advanced through to the knot with the knot pusher instrument. The knot is forced over the end of the tensioner to lock the knot. Subsequent reversing half hitches may be added to secure the knot after the tensioner is removed. The procedure is repeated to secure the other bundle under anatomic tension in the appropriate knee extension/flexion. Button 320 includes four holes, for example, to accommodate strands 305A and B.

Figure 20A:
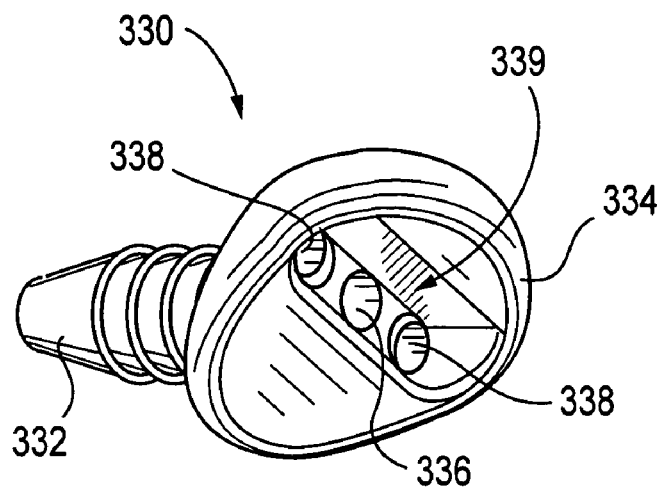
FIGS. 20A–20C illustrate a button implant and driver used to securely fixate the inserted graft.
Figure 20B:
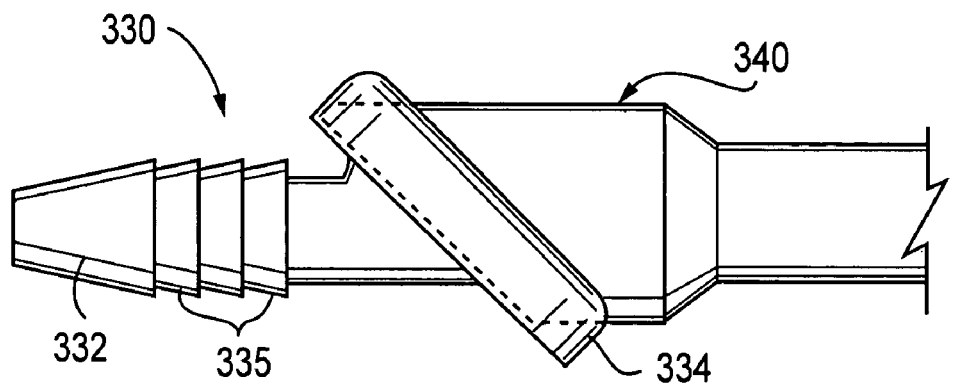
Figure 20C:
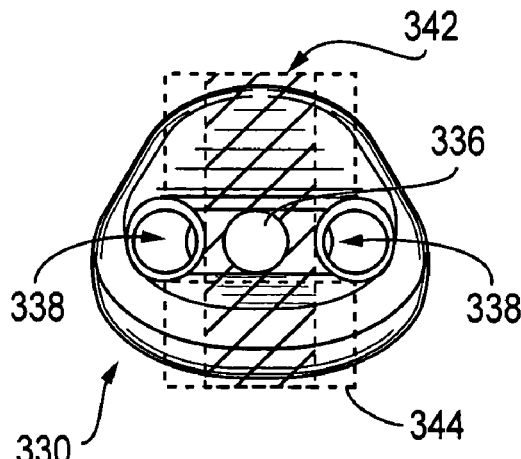

Referring to FIGS. 20A–C, a button implant 330 (sold by the assigned, Arthrex, Inc., under the tradename Tension Lok) is illustrated. Implant 330 is used in place of buttons 310 and 320, for example, in securing tensioned strands at the surface of bone, particularly the femur. Implant 330 includes a ribbed, cannulated body 332 and an angled head 334. A central cannula 336 extends through the implant 330. Ribs 335 are tapered. The head 334 features rounded edges and corners, and has a generally triangular shape, as seen in FIGS. 20A and 20C. Openings 338 formed through the head 334 on either side of the head opening of cannula 336 accommodate suture strands. The openings 338 are formed within a cavity 339 developed in the head 334 to provide a relief for knots tied in suture strands brought through the holes 338. The head 334 is angled, as seen in FIGS. 20A and 20B, to sit flush with the surface of the bone into which it is installed.

Implant 330 is introduced into a bone hole using a driver 340, of which only the distal end and head are shown in FIG. 20B. The head of driver 340 is angled and shaped to complement the head 334 of implant 330. Head 334 occupies a footprint 342 (FIG. 20C) that is narrower than the distance between suture holes 338, as represented by the hatched area 342. Alternatively, head 334 occupies a wider footprint 344 and features a notch on either side providing clear access to suture holes 338.

Although the present invention has been described in relation to particular embodiments thereof, many other variations and modifications and other uses will become apparent to those skilled in the art.

What is claimed is:

1. A method of forming a socket in bone comprising:
   introducing a cannulated guide pin through the bone in an antegrade direction to expose a distal end of the guide pin;
   inserting the distal end of the guide pin through a cannulation in a cutter;
   pulling the cutter into the knee using a strand introduced through the cannulated guide pin and attached to the cutter, to secure the cutter to the distal end of the guide pin; and
   drilling into the bone to create the socket by rotating the cutter and moving the cutter in a retrograde manner using the guide pin,
   wherein the cutter comprises a plurality of cutting teeth radiating symmetrically from a cylindrical body and having edges extending radially from the cannulation.

2. A method according to claim 1, wherein the step of introducing the guide pin includes aligning the guide pin using a drill guide and a marking hook.

3. A method according to claim 2, wherein the marking hook includes a hook tip and a visible mark disposed 5 mm proximal to the hook tip.

4. A method of knee reconstruction comprising:
   forming a socket in a femur in a retrograde manner;
   forming a socket in a tibia in a retrograde manner; and
   securing the ends of a graft respectively in the sockets of the femur and the tibia,
   wherein the step of forming the socket in the femur in a retrograde manner includes introducing a cannulated guide pin through the femur, pulling a retrograde cutter into the knee using a strand introduced through the cannulated guide pin and attached to the cutter, to attach the retrograde cutter to the guide pin, and retrograde cutting into the femur by rotating and withdrawing the guide pin to form the socket in the femur, and
   wherein the cutter comprises a plurality of cutting teeth radiating symmetrically from a cylindrical body.

5. A method according to claim 4, wherein the step of introducing the guide pin through the femur includes aligning the guide pin using a drill guide and an offset marking hook.

6. A method according to claim 5, wherein the step of aligning the guide pin includes using the offset marking hook to align the guide pin 5 mm proximate a distal tip of the offset marking hook.

7. A method of knee reconstruction comprising:
   forming a socket in a femur in a retrograde manner;
   forming a socket in a tibia in a retrograde manner; and
   securing the ends of a graft respectively in the sockets of the femur and the tibia,
   wherein the step of forming the socket in the tibia includes introducing a cannulated guide pin through the tibia, pulling a retrograde cutter into the knee using a strand introduced through the cannulated guide pin and attached to the cutter, to attach the retrograde cutter to the guide pin and retrograde cutting into the tibia to form the retrograde socket in the tibia, wherein the cutter comprises a plurality of cutting teeth radiating symmetrically from a cylindrical body.

8. A method according to claim 7, wherein the step of introducing the guide pin through the tibia includes aligning the guide pin using a drill guide and an offset marking hook.

* * * * *